(12) United States Patent
Bennett

(10) Patent No.: US 6,518,459 B2
(45) Date of Patent: Feb. 11, 2003

(54) PROCESS AND APPARATUS FOR PRODUCING ORGANIC POLYSULFIDES

(75) Inventor: Brooks D. Bennett, Borger, TX (US)

(73) Assignee: Phillips Petroleum Company, Bartlesville, OK (US)

( * ) Notice: Subject to any disclaimer, the term of this patent is extended or adjusted under 35 U.S.C. 154(b) by 14 days.

(21) Appl. No.: 09/915,924

(22) Filed: Jul. 26, 2001

(65) Prior Publication Data

US 2001/0051751 A1 Dec. 13, 2001

Related U.S. Application Data

(62) Division of application No. 09/587,918, filed on Jun. 6, 2000, now Pat. No. 6,284,926.

(51) Int. Cl.$^7$ .................. C07C 321/00; B01D 15/08; B01D 21/01

(52) U.S. Cl. ................ 568/21; 568/26; 210/635; 210/733

(58) Field of Search ............... 568/21, 26; 210/635, 210/733

(56) References Cited

U.S. PATENT DOCUMENTS 6,051,739 A * 4/2000 Shaw ................ 568/26

* cited by examiner

Primary Examiner—Jafar Parsa
(74) Attorney, Agent, or Firm—Charles W. Stewart

(57) ABSTRACT

A filtering means containing gelatinous and solid materials is cleaned without dismantling the filtering means by contacting the gelatinous material inside the filtering means with a solvent, thereby physically degrading the gelatinous material such that the degraded gelatinous material can pass through the filtering means.

9 Claims, 1 Drawing Sheet

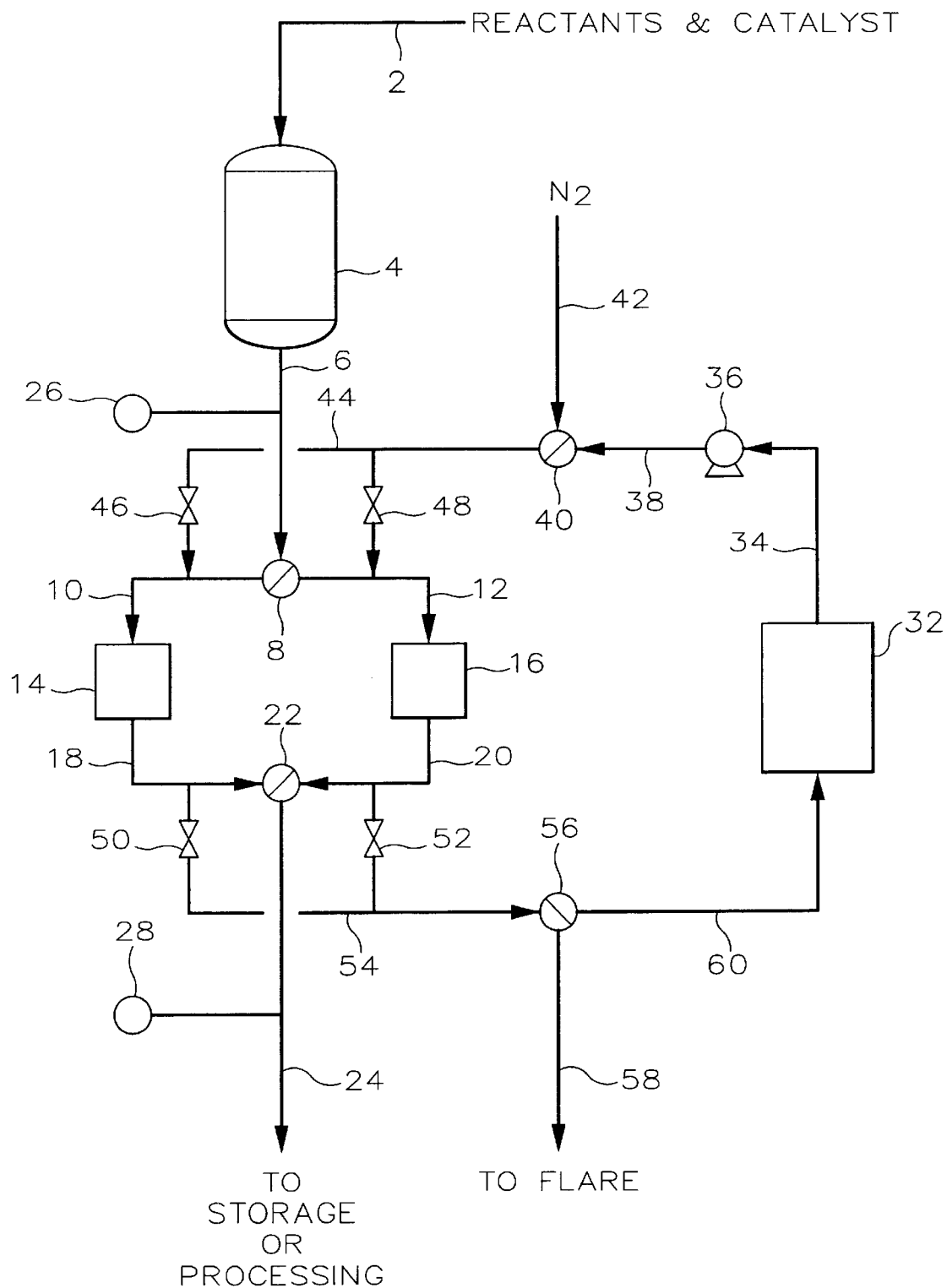

PROCESS AND APPARATUS FOR PRODUCING ORGANIC POLYSULFIDES

This application is a division of application Ser. No. 09/587,918, filed Jun. 6, 2000, now, U.S. Pat. No. 6,284,926.

The present invention relates to an improved process and apparatus for producing organic polysulfides. More particularly, the present invention relates to an improved process and apparatus for removing undesirable byproducts from a crude organic polysulfide product.

BACKGROUND OF THE INVENTION

Organic polysulfides are useful for many purposes such as additives for elastomers, antioxidants for lubricating oils, intermediates for the production of organic chemicals, insecticides, and germicides and additives for diesel fuels to improve cetane number and ignition qualities. Organic polysulfides are also useful in the compounding of high pressure lubricants and in the acceleration of rubber treating processes.

It is known that organic polysulfides can be produced by reacting mercaptans with elemental sulfur in the presence of a basic catalyst. The crude organic polysulfide product produced by such a reaction typically comprises a distribution of various organic polysulfides (for example, disulfides, trisulfides, and tetrasulfides), hydrogen sulfide, at least one solid byproduct, and at least one gelatinous byproduct. Generally, the crude organic polysulfide product is further processed to obtain a purified organic polysulfide product.

One process employed to obtain a purified organic polysulfide product is the removal of the solid and gelatinous byproducts from the crude organic polysulfide product. The solid and gelatinous byproducts are typically removed by passing the crude organic polysulfide product through a filter. Due to the buildup of solid and gelatinous byproducts within the filter, such filter must be cleaned periodically.

The cleaning of the byproduct filter is a labor intensive operation wherein the filter assembly is dismantled and the filtered byproducts are manually removed. In addition, such manual cleaning of the filter is an unpleasant task due to the foul order of the filtered byproducts. Thus, it is desirable to develop an apparatus and process for producing a purified organic polysulfide product which substantially decreases the frequency of required manual cleanings of the byproduct filter.

SUMMARY OF THE INVENTION

An object of the present invention is to provide an improved process and apparatus for producing organic polysulfides.

Another object of the present invention is to provide an improved process and apparatus for removing solid and gelatinous byproducts from a crude organic polysulfide product.

A further object of the present invention is to provide a process and apparatus which substantially decreases the frequency of required manual cleanings of a filter which removes solid and gelatinous byproducts from a crude organic polysulfide product.

Other objects and advantages of the present invention will become more apparent as the invention is more fully disclosed hereinbelow.

According to an embodiment of the present invention, a process is provided comprising the steps of (a) trapping at least one solid material and at least one gelatinous material in a filtering means, (b) contacting the gelatinous material with a solvent to produce a degraded gelatinous material capable of passing through the filtering means, and (c) passing the degraded gelatinous material through the filtering means.

According to a further embodiment of the present invention, an apparatus is provided which comprises (a) a filtering means, (b) a solvent source connected with the filtering means, and (c) a solvent flow control means for controlling the flow of a solvent between the solvent source and the filtering means.

BRIEF DESCRIPTION OF THE DRAWING

FIG. 1 shows a simplified flow diagram of an apparatus and process for producing organic polysulfides in accordance with an embodiment of the present invention.

DETAILED DESCRIPTION OF THE INVENTION

It has been discovered that the efficiency of a process for producing organic polysulfides by reacting a mercaptan and a sulfur compound in the presence of a catalyst can be improved by employing a novel method of cleaning the filtering means which traps solid and gelatinous materials present in the crude organic polysulfide product.

The mercaptan suitable for use as a reactant in such a process of producing a crude organic polysulfide product can be any mercaptan having the formula RSH, wherein R is a hydrocarbyl radical having 1 to about 30, preferably 1 to about 20, and most preferably 2 to 15 carbon atoms. The hydrocarbyl radical can be linear or branched and can be alkyl, aryl, cycloalkyl, alkylaryl, aralkyl, alkenyl radicals, or combinations of two or more thereof. Preferably, the hydrocarbyl radical is an alkyl radical. Presently preferred mercaptans are tertiary mercaptans. The presently most preferred mercaptan is t-butyl mercaptan.

The sulfur compound suitable for use as a reactant in the present process can be any sulfur-containing compound capable of reacting with a mercaptan to produce a crude organic polysulfide product. Preferably, the sulfur compound is elemental sulfur. The amount of sulfur compound contacted with the mercaptan depends on the desired sulfur content and the organic polysulfide product. For an average sulfur content of q sulfurs per polysulfide molecule (q–1) moles of sulfur must be added per 2 moles of mercaptan and 1 mole of hydrogen sulfide will be produced per 2 moles of mercaptans reacted. It is, however, preferred that about 0.5 to about 10, preferably about 1 to about 5, and most preferably 1.0 to 2.0 moles of mercaptan per mole of sulfur is used.

The catalyst suitable for use in the present process can be any catalyst capable of catalyzing the reaction of a mercaptan and a sulfur compound to form a crude organic polysulfide product. The presently preferred catalyst comprises a basic catalyst which can be an inorganic base, an organic base, or combinations of two ore more thereof. Suitable organic bases include, but are not limited to tetramethylammonium hydroxide, tetraethylammonium hydroxide, tetrapropylammonium hydroxide, tetramethylammonium bisulfide, tetraethylammonium bisulfide, trimethylamine, triethylamine, n-butylamine and combinations of two or more thereof. Suitable inorganic bases include, but are not limited to, lithium hydroxide, sodium hydroxide, sodium bisulfide, potassium hydroxide, calcium hydroxide, magnesium hydroxide, sodium bicarbonate, sodium carbonate, sodium oxide, sodium sulfide, magnesium oxide, calcium oxide, calcium carbonate, sodium phenoxide, barium phenoxide, calcium phenoxide, $R_1ONa$, $R_1SNa$, and combinations of any two or more thereof; where $R_1$ is a $C_1$–$C_{18}$ alkyl radical, or combinations of any two or more thereof. Presently, the amine catalysts are not as preferred as other catalysts, and an inorganic base is preferred because of the availability and low cost of inorganic bases. Among the inorganic bases, sodium hydroxide is preferred.

The catalyst useful in the process of the present invention can further comprise a surfactant, preferably an alkoxylated compound, most preferably an alkoxylated alcohol. An alkoxylated alcohol useful in the present invention has a general formula of $R_2O[CH_2CH(R_3)O]_mH$ where $R_2$ is a $C_1$–$C_{20}$ hydrocarbyl radical selected from the group consisting of alkyl radical, alkylaryl radical, aryl radical, cycloalkyl radical, and alkenyl radical. Preferably, $R_2$ is a $C_6$–$C_{18}$ alkyl radical. Most preferably, $R_2$ is a $C_{10}$–$C_{16}$ alkyl radical. Preferably, $R_3$ is selected from the group consisting of hydrogen, $C_1$–$C_{16}$ alkyl radical and $C_2$–$C_{16}$ alkenyl radicals. More preferably, $R_3$ is a hydrogen or a $C_1$–$C_3$ alkyl radical. Most preferably, $R_3$ is hydrogen. Preferably, m is a number from 1 to about 20, more preferably from about 2 to about 12, and most preferably from 5 to 10. An example of a suitable alkoxylated alcohol is TERGITOL® 15-S-7 which is an ethoxylated alcohol, manufactured and marketed by Union Carbide Corporation. Other suitable alkoxylated alcohols are also available from Union Carbide Corporation.

The weight ratio of base to surfactant in the catalyst can vary widely so long as the ratio can catalyze the reaction of a mercaptan and a sulfur compound. Preferably, the weight ratio of a base to surfactant is from about 10:1 to about 1:100, more preferably from about 2:1 to about 1:10, most preferably from 1:1 to 1:5.

The amount of catalyst contacted with the mercaptan and sulfur compound can be any amount capable of catalyzing the formation of a crude organic polysulfide product. The weight of the catalyst as a percentage of the weight of mercaptans can be in the range of from about 0.001 to about 10 percent, preferably from about 0.01 to about 3 percent, and most preferably from 0.05 to 2 percent.

The contacting of the mercaptan, sulfur compound, and catalyst can take place in any suitable reaction vessel. The contacting is generally accomplished by slowly adding one of the reactants to a mixture of the other reactant and the catalyst. The reaction of the mercaptan and sulfur compound can commence at ambient temperatures, but is generally desirable to accelerate the reaction by stirring and/or increasing the temperature of the liquid reaction solution. The reaction temperature can be from about 30° C. to about 250° C., preferably from about 50° C. to about 150° C., more preferable from about 80° C. to about 130° C., and most preferably from 95° C. to 115° C. The reaction pressure can vary widely from about 1 atmosphere to about 20 atmospheres, preferably from about 1 atmosphere to about 10 atmospheres. The period of time required to produce a suitable crude organic polysulfide product is generally from about 0.5 hours to about 20 hours, more preferably from about 1 hour to about 10 hours, and most preferably from about 2 hours to about 5 hours.

The crude organic polysulfide product produced by the above-described reaction of the mercaptan and sulfur compound comprises at least one organic polysulfide, hydrogen sulfide, at least one gelatinous byproduct, and at least one solid byproduct.

The organic polysulfides of the crude organic polysulfide product can be any organic polysulfides having the formula of $RS_xR$, wherein each R can be the same or different and are each a hydrocarbyl radical having 1 to about 30, preferably 1 to about 20, and most preferably 2 to about 15 carbon atoms, and x is a number from 2 to 10, preferably 2 to 6, and most preferably 3 to 5. The hydrocarbyl radical can be linear or branched and can be alkyl, aryl, cycloalkyl, alkylaryl, aralkyl, alkenyl radicals, or combinations of two or more thereof. Preferably, the hydrocarbyl radical is an alkyl radical. Preferred organic polysulfides are di-t-butyl polysulfides. More preferred organic polysulfides include di-t-butyl disulfide, di-t-butyl trisulfide, and di-t-butyl tetrasulfide. The most preferred organic polysulfide is di-t-butyl trisulfide.

The gelatinous byproduct of the crude organic polysufide product can comprise any material or combination of materials having a gelatinous physical nature. The gelatinous byproduct typically comprises a quantity of the surfactant employed in the mercaptan/sulfur reaction as well as small quantities of organic polysulfide compounds.

The solid byproduct of the crude organic polysulfide product can be any solid material or combination of solid materials. Sodium bicarbonate is an example of a common solid material that can be present in a crude organic polysulfide product. Unreacted sulfur compound is a further example of a solid material that can be present in a crude organic polysulfide product.

Subsequent to the above-described reaction, the crude organic polysulfide product can be subjected to a variety of purification, separation, recovery, and stabilization methods to produce a purified organic polysulfide product. A purification process of particular importance in the present invention involves the removal of at least one gelatinous byproduct and at least one solid byproduct from the crude organic polysulfide product.

The removal of the gelatinous and solid byproducts can be accomplished by passing the crude organic polysulfide product through a filtering means. The filtering means can be any filtering means known in the art which is capable of trapping at least a portion of the gelatinous and solid byproducts without trapping more than in insignificant amount of the organic polysulfides. The filtering means preferably comprises at least one filter. More preferably, the filtering means comprises at least one filter having a filtration rating of from about 0.1 microns to about 40 microns. Most preferably, the filtering means comprises two filters, each having a filtration rating of from 0.5 to 10 microns.

One problem associated with using a filtering means to remove the gelatinous and solid byproducts from the crude organic polysulfide product is that flow through the filtering means can rapidly become obstructed by the mixture of the gelatinous byproduct and solid byproduct trapped within the filtering means. In order to detect when the filtering means contains too much trapped byproduct, the pressure drop across the filtering means can be measured during flow of the crude organic polysulfide product through the filtering means. A low pressure drop indicates a relative clean (i.e., free of trapped byproducts) filtering means, while a high pressure drop indicates a relatively plugged filtering means.

When the pressure drop across the filtering means is undesirably high, the filtering means contains too much filtered byproduct and must be cleaned or replaced. The value of the undesirably high pressure drop can vary depending on the maximum differential pressure rating of the filtering means and various preferred operating conditions. Typically, an undesirably high pressure drop is from 50 percent to 100 percent of the maximum differential pressure recommended by the manufacturer of the filtering means.

It has been discovered that when the pressure drop across the filtering means becomes undesirably high, it is advantageous to remove the gelatinous byproduct from the filtering means without manually disassembling the filter. The removal of the gelatinous byproduct can be accomplished by contacting the gelatinous byproduct with a solvent, thereby physically degrading the gelatinous byproduct such that the degraded gelatinous byproduct can pass through the filtering means.

Any solvent capable of physically degrading the gelatinous byproduct can be employed in the inventive process. Preferably, the solvent is an organic solvent. Examples of organic solvents are aromatic hydrocarbons such as benzene, toluene, xylene, and ethylbenzene; aliphatic hydrocarbons such as pentane, hexane, heptane, and octane; alicyclic hydrocarbons such as cyclohexane and methylcyclohexane; halogenated hydrocarbons such as chloroform, dichloromethane, dichloroethane, chlorobenzene, chlorobutane, bromoform, and bromobenzene; alcohols such as methanol, ethanol, 2-propanol, and t-butanol; ketones such as acetone, methyl ethyl ketone, and isobutyl methyl ketone; ethers such as diethyl ether, diisopropyl ether, dibutyl ether, ethylene glycol dimethyl ether, dioxane, and tetrahydrofuran; esters such as ethyl acetate; nitrites such as acetonitrile; and aprotic polar solvents such as sulfur-containing compounds [e.g., sulfoxides (e.g., dimethyl sulfoxide), sulfones (e.g., sulfolane)], N,N-dimethylformamide, and dimethyl sulfoxide. More preferably, the solvent is a ketone. Most preferably, the solvent is acetone.

Prior to contacting the gelatinous byproduct with the solvent, it is preferred to terminate the charging of the crude organic polysulfide to the portion of the filtering means being cleaned with solvent. The gelatinous byproduct within the filtering means can be contacted with the solvent using any suitable method known in the art. The solvent may be contacted with the gelatinous byproduct by conducting the solvent from a solvent source through the filtering means. Preferably, the solvent is circulated by a pump from a solvent tank, through the filtering means, and back to the solvent tank in a closed-loop solvent flow system.

The solvent is contacted with the gelatinous byproduct in the filtering means at a rate and for a time period suitable to remove substantially all gelatinous byproduct from the filtering means. Preferably, the contacting of the solvent with the gelatinous byproduct in the filter continues for a period necessary to restore an adequately low pressure drop across the filtering means when the charging of the crude organic polysulfide product to the filtering means is resumed. An adequately low pressure drop is a pressure drop that is less than the undesirably high pressure drop, described above. Preferably, the adequately low pressure drop is less than 95 percent of the undesirably high pressure drop, more preferably less than 80 percent, and most preferably less than 50 percent.

When the pressure drop across the filtering means is adequately low, a sufficient amount of gelatinous byproduct has been removed from the filtering means and the charging of the solvent to the filtering means can be terminated. Thereafter, the filtering means can be dried by removing residual solvent from the filtering means, in order to prevent contamination of the crude organic polysulfide product with the solvent. Drying of the filtering means can be accomplished using any suitable means known in the art, for example, by purging the filtering means with a suitable drying gas, such as, for example, oxygen and/or nitrogen.

If the contacting of the solvent with the gelatinous material in the filtering means does not provide an adequately low pressure drop, the filtering means is plugged with the solid byproduct and must be manually cleaned or replaced.

Removing the gelatinous byproduct without removing the solid byproduct from the filtering means, in accordance with the present invention, decreases the frequency of required manual cleanings of the filtering means. In addition, because the foul odor generally associated with removing a gelatinous and solid byproduct mixture from the filtering means is caused by the gelatinous byproduct, the manual removal of only the solid byproduct, in accordance with the present invention, is relatively odor-free.

Referring now to FIG. 1. In accordance with an embodiment of the present invention, a mercaptan, sulfur compound, and catalyst are charged to a reactor 4 via a conduit 2. The crude organic polysulfide product produced by the reaction in reactor 4 is conducted from reactor 4 to a three-way valve 8 via a conduit 6. Upstream three-way valve 8 controls the flow of the crude organic polysulfide product to either a conduit 10 or a conduit 12.

The system depicted in FIG. 1 comprises two filters—a filter 14 and a filter 16. Filter 14 and filter 16 are capable of trapping at least a portion of the solid and gelatinous byproducts contained in the crude organic polysulfide product while allowing at least a portion, and preferably substantially all, of the organic polysulfides to pass therethrough. The use of two filters allows for the continuous filtering of the crude organic polysulfide product by allowing one filter to be cleaned while the other filter is receiving the crude organic polysulfide product.

The filtered organic polysulfide product exits filter 14 or filter 16, whichever is receiving the crude organic polysulfide product, into a conduit 18 or a conduit 20. From conduit 18 or conduit 20, the filtered organic polysulfide product is sent to storage or further processing via a three-way valve 22 and a conduit 24.

The cleaning of the filter not receiving the crude organic polysulfide product is accomplished by contacting the contents of such filter with a solvent 30. Solvent 30 is conducted to the filter not receiving crude organic polysulfide product by switching on a pump 36, thereby causing solvent 30 to flow from a solvent tank 32 to the filter not receiving crude organic polysulfide product via a conduit 34, pump 36, a conduit 38, three-way valve 40, and a header 44. The flow of solvent 30 through either filter 14 or filter 16 is controlled by adjusting a valve 46, a valve 48, a valve 50, and a valve 52. After passing through the filter not receiving crude organic polysulfide product, solvent 30 is returned to solvent tank 32 via header 54, a three-way valve 56, and a conduit 60. The circulation of solvent 30 from solvent tank 32 to the filter not receiving the crude organic polysulfide product is continued until such filter is cleaned of substantially all trapped gelatinous byproduct. Thereafter, pump 36 is turned off, and residual solvent 30 is removed from the filter not receiving the crude organic polysulfide product by purging with nitrogen.

The process of purging the filter with nitrogen is commenced by adjusting a three-way valve 40 and a three-way valve 56 to allow nitrogen to flow to the filter not receiving the crude organic polysulfide product via a conduit 42, three-way valve 40, and header 44. The flow of nitrogen to either filter 14 or filter 16 is controlled by valve 46, valve 48, valve 50, and valve 52. After flowing through the filter not receiving the crude organic polysulfide product, the nitrogen is sent to a flare via header 54, three-way valve 56, and a conduit 58.

After being cleaned and purged, the filter not receiving the crude organic polysulfide product is ready to receive the crude organic polysulfide product.

To determine when the flow of the crude organic polysulfide product should be switched from one filter to the other, the pressure drop across the filter is measured using an upstream pressure gauge 26 and a downstream pressure gauge 28. When the pressure drop across the filter receiving the crude organic polysulfide product is undesirably high (i.e., the filter is plugged), three-way valve 8 and three-way valve 22 are adjusted to cause the crude organic polysulfide product to flow through the non-plugged filter. Once flow is diverted to the non-plugged filter, the plugged filter can be cleaned in accordance with the above-described process.

The above described filtering, cleaning, and purging process is repeated until the cleaning of filter 14 or filter 16 with solvent 30 no longer provides an adequately low pressure drop across the filter, thereby indicating that the filter is plugged with solid byproduct. At that point, all flow to the plugged filter is terminated, the plugged filter is dismantled, and the byproducts located therein are removed. After the byproducts are removed, the manually cleaned filter is reassembled, and charging of the crude organic polysulfide product to the manually cleaned filter is resumed.

The following examples are provided to further illustrate the practice of the present invention and are not intended to limit the scope of the invention of the claims.

EXAMPLE I

The following example demonstrates a conventional method of preparing organic polysulfides by reacting a mercaptan and a sulfur compound in the presence of a basic catalyst and, thereafter, removing a gelatinous byproduct and a solid byproduct from the crude organic polysulfide product.

In a batch reaction process, a crude organic polysulfide was produced by reacting about 585 pounds of t-butyl mercaptan and about 135 pounds of flour sulfur in the presence of about 200 grams of 50% sodium hydroxide and about 200 grams of TERGITOL® 15-S-7 ethoxylated alcohol (Union Carbide Corporation; Danbury, Conn.). The reaction took place in a 100 gallon Hastelloy C reactor.

During the reaction, the reactor contents were stirred. Reaction conditions included a reaction temperature of about 105° C. and a reaction pressure which varied from about 0 psig to about 135 psig due to the buildup and venting of hydrogen sulfide. The reaction period was approximately 3 hours.

After the reaction period, the crude organic polysulfide product was passed through a Cuno model CT101 filter housing containing a 5 micron Cuno model DPPTB1 filter cartridge (Cuno Incorporated; Meriden, Conn.). The pressure drop across the filter was monitored as the crude organic polysulfide product flowed through the filter. When the pressure drop across the filter was 30 psi, flow of the crude organic polysulfide product to the filter was terminated. The filter was disassembled, the filter contents were manually removed, and a foul odor associated with the filter contents was detected.

The filter contents were weighed. The total weight of the filter contents was 160 grams, with 40 grams being attributable to a byproduct of gelatinous nature, and 120 grams being attributable to a byproduct which was solid in nature.

EXAMPLE II

The following example demonstrates the inventive method of preparing organic polysulfides by reacting a mercaptan and sulfur in the presence of a basic catalyst, and thereafter passing the crude organic polysulfide product through a filter which was cleaned by contacting its contents with a solvent.

The crude organic polysulfide product employed in the present example was produced using substantially the same process described in Example I.

As in Example I, the crude organic polysulfide product was passed through a Cuno model CT101 filter housing containing a 5 micron Cuno model DPPTB1 filter cartridge, having a 30 psi maximum pressure differential. When the pressure drop across the filter was about 30 psi, the flow of the crude organic polysulfide product was terminated, but the filter was not disassembled. Rather, acetone was circulated through the filter by charging a tank with 65 pounds of acetone, pumping acetone to the filter inlet, and returning the acetone to the tank in a closed-loop flow system. Acetone was allowed to circulate through the system for about 20 minutes. The acetone pump was then turned off and residual acetone was removed from the filtering means by purging with nitrogen. Flow of the crude organic polysulfide product through the filtering system was then resumed.

The process of (1) charging the crude organic polysulfide product to the filter, (2) monitoring of the pressure drop, (3) cleaning of the filtering system with acetone, and (4) purging with nitrogen was repeated until the filter was sufficiently full of solid byproducts such that the acetone cleaning was ineffective to restore an adequately low pressure drop (less than about 25 psi) across the filter. At that point, the filter was disassembled, and the filter contents were manually removed. No foul odor was detected with the filter contents.

The filter contents were weighed. The total weight of the filter contents was 760 grams, all of which was attributable to byproducts which were solid in nature.

The inventive method of Example II allowed for the time between manual cleanings of the filter to be extended by approximately six-fold over the conventional process of Example I, because the filter cleaned by the inventive process was able to trap 760 grams of solid byproduct prior to a required manual cleaning, while the filter cleaned by the conventional method was only able to trap 120 grams of solid byproduct prior to a required manual cleaning. In addition, there was no foul odor associated with manually cleaning the filter which had been cleaned in accordance with the inventive process.

While this invention has been described in detail for the purpose of illustration, it should not be construed as limited thereby but intended to cover all changes and modifications within the spirit and scope thereof.

That which is claimed is:

1. A process comprising:
   (a) trapping at least one solid material comprising sodium bicarbonate and at least one gelatinous material comprising organic polysulfide in a filtering means;
   (b) contacting said at least one gelatinous material with a solvent to produce a degraded gelatinous material capable of passing through said filtering means; and
   (c) passing said degraded gelatinous material through said filtering means.

2. A process according to claim 1, wherein said at least one gelatinous material comprises a surfactant.

3. A process according to claim 2 wherein said solvent is an organic solvent.

4. A process according to claim 3 wherein said filtering means comprises at least one filter.

5. A process according to claim 4 wherein said at least one solid material further comprises a sulfur compound.

6. A process according to claim 5 wherein said solvent is selected from the group consisting of aromatic hydrocarbons, aliphatic hydrocarbons, alicyclic hydrocarbons, halogenated hydrocarbons, alcohols, ketones, ethers, esters, and aprotic polar solvents.

7. A process according to claim 6 wherein said filtering means comprises at least one filter having a filtration rating of from about 0.1 microns to about 40 microns.

8. A process according to claim 6 wherein said solvent comprises a ketone.

9. A process according to claim 8 wherein said filtering means comprises two filters, each having a filtration rating of from 0.5 microns to 20 microns.

* * * * *